United States Patent [19]

Wilkins et al.

[11] Patent Number: 4,879,218

[45] Date of Patent: * Nov. 7, 1989

[54] ANTIBODY FOR *C.DIFFICILE*

[75] Inventors: Tracy D. Wilkins, Blacksburg; David M. Lyerly, Radford, both of Va.

[73] Assignee: Virginia Tech Intellectual Properties, Inc.

[*] Notice: The portion of the term of this patent subsequent to Aug. 6, 2002 has been disclaimed.

[21] Appl. No.: 211,070

[22] Filed: Jun. 20, 1988

Related U.S. Application Data

[63] Continuation of Ser. No. 740,419, Jun. 3, 1985, abandoned, which is a continuation-in-part of Ser. No. 683,150, Dec. 18, 1984, abandoned, which is a continuation-in-part of Ser. No. 417,379, Sep. 13, 1982, Pat. No. 4,533,630.

[51] Int. Cl.$^4$ ................ G01N 33/535; G01N 33/577
[52] U.S. Cl. .......................................... 435/7; 435/21; 435/68; 435/172.2; 435/240.27; 435/842; 435/948; 436/518; 436/548; 530/387; 935/103; 935/110
[58] Field of Search ............... 435/7, 21, 68, 172.2, 435/240.27, 842, 948; 436/518, 548; 935/103, 110; 530/387

[56] References Cited

U.S. PATENT DOCUMENTS

| | | | |
|---|---|---|---|
| 4,361,647 | 11/1982 | Remington et al. | 435/108 |
| 4,376,110 | 3/1983 | David et al. | 436/513 |
| 4,530,833 | 7/1985 | Wilkins et al. | 424/88 |
| 4,533,630 | 8/1985 | Wilkins et al. | 435/7 |

OTHER PUBLICATIONS

Laughon et al., J. Infect. Dis., vol. 149(5), May 1984, 781–88.
Viscidi et al, J. Clin. Microbiol., 18(2), Aug. 1983, 242-7.
Wilkins et al, Ciba Found Symp. (Netherlands), v. 112, pp. 230–241, 1985 (abstract only).
Lyerly et al, J Clin Microbiol, v. 21(1), pp. 12–15, 1985 (abstract only).

*Primary Examiner*—Christine M. Nucker
*Attorney, Agent, or Firm*—Elloit M. Olstein; Raymond J. Lillie

[57] ABSTRACT

Monoclonal antibody to toxin A of *C.difficile* has been prepared and is used in an assay for toxin A of *C.difficile*.

34 Claims, No Drawings

ANTIBODY FOR C.DIFFICILE

This application is a continuation of U.S. application Ser. No. 740,419 abandon and continuation-in-part of U.S. application Ser. No. 683,150' abandoned and 417,379' U.S. Pat. No. 4,533,630 filed on June 3, Dec. 18, 1984 and Sept. 13, 1982 respectively.

This invention relates to C. difficile and more particularly to the production of antibodies to a toxin of C. difficile, and the use thereof in n assay for C. difficile toxins.

The anaerobic organism Clostridium difficile (C. difficile) is associated with antibiotic related pseudomembranous colitis and as a result, there have been tests developed to ascertain the presence of C. difficile antigen in specimens of human stool.

One such test involves culture of human feces, which requires specialized facilities and a long period of time. This test also detects strains of C. difficile that do not produce toxins, and thus gives false positive results.

Another test involves counter immunoelectrophoresis, however, this test, as currently used, is not sensitive enough to detect toxins and gives a lot of false positives.

A further test involves an enzyme immunoassay; however, many tests currently used do not differentiate between toxic and non-toxic strains, and as a result, such test may give misleading results.

The present invention is directed to antibodies for toxin A of C. difficile, and an assay for toxigenic C. difficile.

In accordance with one aspect of the present invention, there is provided a monoclonal antibody for toxin A of C. difficile, and such monoclonal antibody supported on a solid support.

In accordance with yet another aspect of the present invention, there is provided an assay for toxin A of C. difficile which uses monoclonal antibody for toxin A.

In accordance with a further aspect of the present invention, there is provided a hybridoma for toxin A of C. difficile which is capable of producing a monclonal antibody to C. difficile. More particularly, the present invention is directed to a monoclonal antibody to toxin A of C. difficile which is mono-specific for a single determinant site on toxin A of C. difficile, and in particular human toxin A, and to the hybridoma which produces such antibody.

The hybridoma was prepared generally following the method of Milstein and Kohler [Nature 256, 495-97 (1975)]. The method of producing the hybridoma generally includes the following steps:

1. Immunizing mice with toxin A of C. difficile, preferably Balb/C mice, although other strains may be employed.

2. Removal of the spleen cells and fusion with myeloma cells from a mouse. Such cells are generally those that will not survive in a selective medium in which the hybridoma will survive. In general, the fusion promoter is polyethylene glycol, although other fusion promoters may be used.

3. Culturing of fused and unfused cells in a selective media which will not support the growth of unfused cells to kill unfused cells. The unfused myeloma cells perish and unfused spleen cells which have a finite life also perish.

4. Evaluating the supernatant in each well containing a fused cell (hybridoma) for the presence of antibody to toxin-A of C. difficile and selecting and cloning the hybridomas producing the desired antibody.

After selecting and cloning the hybridoma, the antibody may be produced either by in vitro culturing followed by recovery of the desired antibody from the supernatant or by injecting the hybridoma into mice to produce tumors which result in a high concentration of the monoclonal antibody in the blood and ascites fluid. As generally known in the art, the in vitro method generally does not produce a high quantity and/or concentration of antibody, whereby monoclonal antibody is generally produced in ascites fluid of mice.

The production of hybridoma and monoclonal antibody will be further described with respect to the following examples; however, the scope of the invention is not to be limited thereby:

Example I

Preparation of vaccines for immunization of mice

A. Vaccine 1: C. difficile VPI 10463 was grown in brain heart infusion dialysis flasks at 37° C. for 2 days. The cells and debris were removed by centifugation and the supernatant fluid was passed through a 0.45 um membrane. The filtered material, representing the culture filtrate, was inactivated by adding 1/100 volume of 40% formalin to the filtrate and incubating the mixture at 37° C. overnight. The inactivated filtrate was mixed with an equal volume of incomplete Freund adjuvant for the preparation of the vaccine.

B. Vaccine 2: Culture filtrate from C. difficile V.P.I. 10463 was prepared as described for vaccine 1. Toxin A in the culture filtrate was purified to homogeneity by $(NH_4)_2SO_4$ precipitation, ion-exchange chromatography, and precipitation in acetate buffer. The toxin was inactivated by adding 1/100 volume of 40% formalin to the toxin and incubating the mixture at 37° C. overnight. The inactivated toxin A (toxoid A) was mixed with an equal volume of incomplete Freund adjuvant for the preparation of the vaccine.

EXAMPLE II

Preparation of toxin A. Toxin A was purified to homogeneity from culture filtrates of C. difficile strain 10463 as previously described: Sullivan, N.M., S. Pellet, and T.D. Wilkins. 1982 Purification and characterization of toxins A and B of Clostridium difficile. Infect. Immun. 35:1032-1040.

The toxin was inactivated with 0.4% formalin.

Production of monoclonal antibody. (i) Immunization. Balb/c mice (Dominion Laboratories, Dublin, VA) were immunized with toxoid A (Vaccine 1) mixed 1:1 with incomplete Freund adjuvant. The mice received 0.1 mg of toxoid intraperitoneally once every two weeks for 10 weeks. Each animal received 0.5 mg of toxoid A without adjuvant intraperitoneally 4, 3, and 2 days before splenectomy (ii) Fusion. Spleen cells from immunized mice were fused with myeloma cells using the polyethylene glycol fusion method; Galfre, G., and C. Milstein. 1981. Preparation of monoclonal antibodies: strategies and procedures. In J. J. Langone and H. Van Vunakis (ed.), methods in Enzymology. Academic Press, Inc., New York. Hybrid cell lines were selected in RPMI 1640 medium (Gibco Laboratories, Grand Island, NY) containing hypoxanthine-aminopterin-thymidine and their culture supernatant fluids were analyzed for toxin A antibody by the screening ELISA described below. Hybrids which were positive for toxin a antibody were subcloned in soft agar.

(iii) Production of ascites fluid. About 1 to $2 \times 10^6$ toxin A antibody-producing hybrid cells of each selected clone were injected intraperitoneally into Balb/c mice primed with pristane. Ascites fluid was clarified by centrifugation and brought to 50% saturation by the dropwise addition of a solution of 100% saturated $(NH_4)_2SO_4$. The precipitate was collected by centrifugation, dissolved in phosphate-buffered saline (PBS) to the original sample volume, and dialyzed against PBS. The preparation was passed through a 0.45 um membrane and stored at 4° C.

EXAMPLE III

Screening ELISA. Wells of microtiter plates (Immulon type 1; Dynatech Laboratories, Inc., Alexandria, VA) were coated with 0.5 ug amounts (2.5mg/ml) of toxin A in carbonate buffer, pH 9.6. The plates were incubated overnight at 37° C. and each well was washed once with 0.25 ml of phosphate-buffered saline (PBS) containing 0.05% Tween 20 (PBS-T) and 0.1% bovine albumin. Samples (0.1 ml) of culture supernatant fluid from wells with hybridomas were added and the plates were incubated for 1h at 37° C. The plates were washed five times with PBS-T and 0.2 ml of rabbit anti-mouse IgG-alkaline phosphatase conjugate (Kirkegaard and Perry Laboratories, Inc., Gaithersburg, MD) diluted 1/500 in PBS-T was added. Following incubation for 1 h at 37° C., the plates were washed five times with PBS-T and 0.2 ml of a 1 mg/ml solution of p-nitrophenylphosphate (Sigma Phosphatase 104 substrate) in diethanolamine buffer, pH 9.6, was added to each well. The plates were incubated for 30 min at room temperature, and examined for positive reactions. Controls included adding RPMI 1640 medium and SP2/0 culture supernatant fluid in place of hybridoma culture supernatant fluid.

EXAMPLE IV

Determination of isotype of monoclonal antibodies. Hybridoma culture supernatant fluid was concentrated ten-fold on a B125 minicon unit (Amicon Corp., Danvers, MA). Samples (10 ul) of the concentrated fluid were tested by Ouchterlony double immunodiffusion for immunoreactivity against samples (10 ul) of heavy chain and light chain-specific rabbit anti-mouse antisera (Litton Bionetics, Inc., Charleston, SC).

The hybridoma and monoclonal antibody produced in the previous examples were each designated PCG-4. The monoclonal antibody PCG-4 was determined to be isotype or subclass Ig $G_{2a}$kappa chain isotype.

Antibody PCG-4 had the novel characteristic that it immunoprecipitated toxin A. The estimated molecular weight, as determined by polyacrylamide gel electrophoresis is about 160,000.

EXAMPLE V

Repeating the above procedure of Examples I-IV there was also produced a hybridoma and monoclonal antibody designated as PBA 3. The monoclonal antibody PBA 3 was determined to be of isotype or subclass Ig G 1. Antibody PBA 3 had the novel characteristic that it immunoprecipatated toxin A. The estimated molecular weight, as determined by polyacrylamide gel electrophoresis is about 160,000.

The antibodies also have the following chracteristics:

1. The antibodies neutralize in vitro the enterotoxic activity of toxin A as demonstrated in hamsters. For this neutralization test, the antibody (either PBA-3 or PCG-4) is mixed with an amount of toxin A. This mixture is then given to hamsters with a gavage needle (i.e., the mixture is put into the stomach by catheterization). Normally, the amount of toxin used in the assay will cause diarrhea (i.e., the enterotoxic activity) and death in the hamsters. However, the PBA-3 and PCG-4 antibodies each neutralize this activity.

2. The antibodies prevent the binding of toxin A to rabbit erythrocytes. We have found that toxin A readily binds to rabbit erythrocytes (H. C. Krivan and D. M. Lyerly, 1985, Abstr. Amer. Soc. Microbiol., p. 39, B125 and p. 340, C245). If sufficient amounts of toxin A are present, the toxin will actually agglutinate the erythrocytes. However, if only small amounts of the toxin are present, additional toxin A antibody is needed to agglutinate the erythrocytes. This occurs as follows. The small amount of toxin which is present binds to the erythrocytes; however, small amounts of toxin will not agglutinate the erythrocytes. Toxin A antibody is then added and agglutinates the erythrocytes via the toxin bound to the erythrocytes. The PCG-4 and PBA-3 antibodies each prevent the erythrocytes from agglutinating when the additional toxin A antibody is added; thus, the PCG-4 and PBA-3 antibodies prevent toxin A from ini-tially binding to the erythrocytes.

3. Toxin A is inactivated by oxidizing agents, including N-bromo-succinimide and $H_2O_2$ (D. M. Lyerly, M. D. Roberts, and H. C. Krivan, 1985, Abstr. Amer. Soc. Microbiol., p. 39, B126). Apparently, these agents alter the structure of the toxin. When the toxin is oxidized with these agents, the PBA-3 and PCG-4 antibodies no longer react with the toxin. We have shown this using immunoassays similar to the direct immunoassay described above. These findings indicate that the oxidizing agents destroy the site on the toxin to which the PBA-3 and PCG-4 antibodies bind.

In addition, antibodies PBA 3, and PCG-4, completely inhibit each other from binding to toxin A, which indicates that each is directed against the same or similar portion or site of the toxin A molecule.

Hybridomas PBA 3, and PCG-4, were deposited at the American Type Culture Collection 12301 Parklawn Drive, Rockville, Md. and were given, respectively accession number ATCC No. HB 8713 and ATCC No. HB 8712.

It is to be understood that the present invention is not limited to the hereinabove described hybridomas and monoclonal antibodies. The present invention encompasses all monoclonal antibodies which are specific for toxin A of C. difficile and all hybridomas which produce such monoclonal antibodies. Although the monoclonal antibodies have been described with respect to certain characteristic sub-classes or isotypes, the present invention is not to be limited thereby. For example, antibodies PCG-4 and PBA-3 are of different sub-classes; however, such difference does not affect the selectivity of the antibody for a specific site. Similarly, although the invention has been described with respect to certain hybridomas, those skilled in the art can produce other hybridomas from the teachings of the invention which will produce monoclonal antibodies having the described characteristics. Such hybridomas are also within the spirit and scope of the invention.

The monoclonal antibodies to toxin A of C. difficile may be used in an assay for C. difficile; and in particular, toxin A of *C. difficile*. The monoclonal antibodies may be used alone or in admixture with each other or in admixture with one or more polyclonal antibodies for *C. difficile* which may or may not be mono-specific for toxin A.

The term "mono-specific antibody for toxin A", as used herein, means an antibody which does not have any determinant sites for antigens of *C. difficile* other than toxin A. The mono-specific antibody may be either a monoclonal antibody or a polyclonal antibody.

"*C. difficile* antibody" or "antibody to *C. difficile*" means antibody which is not mono-specific, and which therefore is comprised of a mixture of antibodies, which includes antibodies for toxins of *C. difficile* (antibody for toxin A and antibody for toxin B) and antibodies for non-toxins of *C. difficile*.

"Antibody for toxigenic *C. difficile*" or "antibody specific for toxins of *C. difficile*" means antibody which does not have determinant sites for antigens of *C. difficile* other than toxin A and toxin B (a mixture of antibody specific only for toxin A and antibody specific only for toxin B).

The term "polyclonal antibody for *C. difficile*" includes a polyclonal antibody for *C. difficile* which is mono-specific for toxin A and a polyclonal antibody for *C. difficile* antigens which is not mono-specific for toxin A.

The mono-specific antibody for toxin A of *C. difficile* and the mono-specific antibody for toxin B of *C. difficile* may be prepared by several different procedures.

In accordance with one procedure, *C. difficile* culture supernatant fluids produced by a known cultivating procedure are boiled to destroy all heat-labile protein antigens (toxin and non-toxin antigen) and thereby provide material containing only the heat-stable antigens of *C. difficile*. These antigens are then supported on a first cyanogen bromide activated Sepharaose column.

Partially purified toxin A and partially purified toxin B, each obtained by elution from a DEAE chromatographic column, as hereinafter described, are coupled to a second and third cyanogen bromide activated Sepharaose column, respectively.

Antibodies to crude *C. difficile* antigens toxin (such toxin includes both toxin A and toxin B as well as many other antigens produced by the bacterium) are produced in a suitable animal; e.g. goats, and the elicited antibody is comprised of an antibody mixture to *C. difficile* antigens (such antibody mixture includes antibodies for toxin A and toxin B, as well as antibodies to the non-toxin antigens, including antibodies to the heat-stable antigens.) The non-toxin antibodies (except the antibodies to the non-toxin heat-stable antigens) are removed from the antibody mixture by contact with whole cells of a non-toxic strain of *C. difficile* to thereby bind the antibodies to non-toxins except for the antibodies to the nontoxic heat-stable antigens.

Subsequently, the antibody mixture (which now contains the antibodies for the toxins, and the antibodies to the non-toxic heat-stable antigens) is then applied to the first column on which the heat-stable antigens of *C. difficile* are supported, whereby the antibodies to the heat-stable antigens become bound.

The mixture which is free of antibody against the heat-stable antigens and contains antibodies to toxins A and B is then divided into two parts, with one part being applied to the second column on which pure toxin A is supported, and the other part being applied to the third column on which partially purified toxin B is supported, whereby in the second column, the antibody to toxin A becomes selectively bound to the supported toxin A and in the third column, the antibody to toxin B becomes selectively bound to the supported toxin B.

The antibodies for toxin A and the antibodies for toxin B are each subsequently eluted from the second and third columns, respectively; e.g., by the use of potassium thiocyanate to thereby, respectively, produce mono-specific antibody for toxin A and mono-specific antibody for toxin B.

Alternatively, mono-specific antibody to toxin A may be produced by applying the crude *C. difficile* antibody onto a column support with immobilized pure toxin A. The non-toxin A antibodies are removed from the column by extensive washing and the remaining antibodies, which are attached to the toxin A, are eluted with potassium thiocyanate.

Alternatively, mono-specific antibody to toxin A may be produced from purified toxin A, prepared as hereinafter described, by injecting toxin A (mixed with some formaldahyde to decrease toxicity without destroying antigenicity or neutralized with antibody) into a suitable animal; e.g. a goat. The mono-specific antibody to toxin A is then recovered by the procedure described in the preceding paragraph.

The mono-specific antibodies of the present invention may be supported on a solid support for use in an assay for *C. difficile*. Alternatively, such antibodies may be used in such an assay in an unsupported form.

Toxin A, which has been partially purified by separation from toxin B, and which still includes some non-toxic proteins may be further purified to produce pure toxin A. The pH and molarity of an aqueous solution of toxin A are adjusted to precipitate toxin A, without precipitating the remaining proteins, whereby pure toxin A is recovered.

More particularly, the pH of the aqueous solution is adjusted to a pH of less than 6.0 and at which toxin A precipitates without precipitation of other proteins or denaturation of the toxin, and the molarity of the aqueous solution is adjusted to less than 0.1M and at which toxin A precipitates without precipitation of other proteins. In general the pH is at least 5.0, with the pH preferably being from 5.3 to 5.7, with the best results being achieved at pH 5.5. The molarity of the solution is generally at least 0.001M, with best results being achieved at 0.01M.

The molarity and pH may be achieved by using a suitable salt buffer; e.g., a sodium acetate buffer. The adjustment of molarity may be conveniently achieved by dialysis, although other procedures are applicable.

The precipitated pure toxin A is recovered from the aqueous solution and may be solublized in water at a buffered pH of about 7.5.

The partially purified toxin A, which is purified to produce pure toxin A may be recovered by procedures generally known in the art. For example, the supernatant from a cell culture of a toxigenic *C. difficile* strain is concentrated with an ultrafiltration membrane that retains only large molecules (over 100,000 M.W.) and the retained material is applied to a chromatographic column. The column (DEAE) is then eluted with gradients of sodium chloride (the first gradient is 0.05–0.25M NaCl with a 0.3M NaCl wash and the second gradient is 0.3–0.6 NaCl), with the first gradient eluting toxin A and the second gradient toxin B.

The monoclonal antibody for toxin A may be supported on a solid support for use in an assay for *C.*

*difficile.* Alternatively, such antibody may be used in such an assay in an unsupported form.

In using a solid support, the solid support may be any of a wide variety of solids, and may be employed in any one of a wide variety of forms; e.g. plates, trays, particles, tubes, sheets, etc.

As representative examples of suitable supports, there may be mentioned: synthetic polymer supports, such as polystyrene, polypropylene, substituted polystyrene (e.g. aminated or carboxylated polystyrene), polyacrylamides, polyamides, polyvinylchloride, etc.; glass beads, agarose; etc. The supports may include reactive groups, e.g. carboxyl groups, amino groups, etc. to permit direct linking to the support.

An antibody of the present invention may be supported on a solid support in a variety of ways; for example, by adsorption, covalent coupling, activation of a suitable support, with protein A, etc.

As representative examples of suitable coupling agents there may be mentioned: dialdehydes; for example glutaraldehyde, succinaldehyde, malonaldehyde, etc.; unsaturated aldehyde, e.g., acrolein, methacrolein, crotonaldehyde, etc.; carbodiimides, diisocyanates; dimethyladipimate; cyanuric chloride etc. The selection of a suitable coupling agents there may be mentioned: dialdehydes; for example glutaraldehyde, succinaldehyde, malonaldehyde, etc.; unsaturated aldehyde, e.g., acrolein, methacrolein, crotonaldehyde, etc.; carbodiimides, diisocyanates; dimethyladipimate; cyanuric chloride etc. The selection of a suitable coupling agent should be apparent to those skilled in the art from the teaching herein.

In accordance with an aspect of the present invention, monoclonal antibody of the present invention may be used in an assay for toxin A.

In some of such assays, one or more of such substances are used in a "labelled" or "tagged" form, and such labels or tags are of a type known in the art for use in assays. Thus, for example, the label or tag may be a radioactive substance, such as radioactive iodine, radioactive cobalt, tritium, etc.; an enzyme; a fluorescent material; a chemiluminescent material, etc.

The labels may be added to the various substances by procedures as generally practiced in the art. Similarly, the label or tag may be detected by procedures known in the art; for example, counters for radioactive labels, colorimetric detection of enzymes, etc.

Monoclonal antibodies of the present invention may be used in supported and/or unsupported form for the assay of *C. difficile.*

In accordance with one embodiment of the invention, there is provided an assay for toxin A of *C. difficile* by use of a monoclonal antibody for toxin A.

In accordance with one aspect of this embodiment, antibody to *C. difficile* is supported on a solid support; for example, a microtiter plate. The supported *C. difficile* antibody is then contacted with a sample to be analyzed (analyte) such as a dilution of patient feces, and as a result of such contact, any toxin A present in the analyte, as well as other antigens of *C. difficile*, become bound to the supported *C. difficile* antibody. Subsequently, the bound analyte protion is contacted with monoclonal antibody for toxin A of *C. difficile*, and such monoclonal antibody is only bound by any toxin A present in the bound analyte portion.

This monoclonal antibody may itself be labelled with an enzyme, fluorescent material, or radioactive material as described previously, and the presence of toxin A can be determined by detecting the presence of this label. Alternatively, the monoclonal antibody bound to toxin A can be detected by use of labelled antibody specific for antibody of the animal in which the monoclonal antibody was raised (in particular goat anti-mouse IgG.); this binds to the monoclonal antibody attached to toxin A. This method is referred to in the art as a double antibody sandwich form of the ELISA assay.

The presence of toxin A in the analyte may be determined by its interaction with monoclonal toxin A antibody in the assay.

In another assay for toxin A of *C. difficile*, monoclonal antibody for toxin A may be supported on a solid support; for example, a microtiter plate, and the supported monoclonal antibody for toxin A is contacted with analyte suspected of containing toxin A, whereby any toxin A present in the sample (and only toxin A) becomes bound to the supported monoclonal antibody. The presence and/or amount of bound toxin A may then be determined by contacting the bound toxin A with *C. difficile* antibody, in labelled form, with such labelled antibody being bound by any bound toxin A. The presence and/or amount of toxin A present in the analyte is then determined by determining the presence and/or amount of the bound labelled antibody. The labeled antibody may be a monoclonal antibody to toxin A. In such procedure there is provided a two site assay which uses both supported monoclonal antibody and labeled monoclonal antibody.

In accordance with a further assay for toxin A, The analyte containing or suspected of containing toxin A, is contacted with a solid support, such as a microtiter tray so that at least the toxin A in the analyte is supported on the solid support. The presence of this toxin A is then detected by monoclonal antibody for toxin A. The supported toxin A selectvely binds only the monoclonal antibody for toxin A. Thus, the monoclonal antibody is supported on a solid support through the supported toxin A of the analyte. This antibody can have a label, such as an enzyme attached, that will allow its detection or a labelled antibody can be used that reacts with the antibody bound to the toxin A (sandwich ELISA method). The presence and/or amount of bound labelled antibody is a measure of the presence or amount of toxin A in the analyte.

In accordance with a still further assay, toxin A may be detected by an agglutination procedure. According to such procedure, solid particles sensitized with monoclonal antibody to toxin A are contacted with analyte containing or suspected of containing toxin A with the presence of toxin A causing agglutination of such particles.

In accordance with still another assay, toxin A may be determined by an inhibition of agglutination procedure by contacting solid particles sensitized with purified toxin A (or sensitized with crude *C. difficile* toxin, which includes toxin A) with both analyte containing or suspected of containing toxin A, and monoclonal antibody for toxin A of *C. difficile*, with the presence of toxin A in the analyte inhibiting agglutination of the sensitized particles by the monoclonal antibody.

In accordance with a particularly preferred aspect, in the above described assay procedures, the antibody used in the assay is a mixture of monoclonal antibody for toxin A and polyclonal monospecific antibody for toxin A.

The use of a mixture of monospecific antibody and monoclonal antibody for toxin A in an assay improves the sensitivity of the assay. The relative proportions of the two antibodies will vary depending on the desired sensitivity and assay conditions; however, in general, the ratio of monoclonal antibody for toxin A to monospecific antibody is in the order of from 1:1 to 1:9; preferably from 2:3 to 3:2.

When using a mixture of antibody in the assay, the labeled antibody would also be a mixture; i.e., mixture of labeled goat anti-mouse IgG and labeled rabbit anti-goat IgG.

The present invention will be further described with respect to the following examples.

EXAMPLE VI

Assay for *Clostridium difficile* Toxin A (1) Add 200 ul of 1/10,000 dilution (in carbonate buffer, pH 9.6) of rabbit antiserum (antibody to *C. difficile*) to each well of a Dynatech Immulon type 2 microtiter plate. Incubate at 4° C. overnight.

(2) Empty plate and add 200 ul of PBS-T containing 0.5% bovine serum albumin to each well. Incubate plate at 37° C. for 30 minutes.

(3) Empty plate and add 200 ul of PBS-T to each well. Incubate plate at room temperature for 5 minutes.

(4) Empty plate and add 200 ul of sample dilution or toxin dilution (1:2) in PBS-T to wells. Incubate plate either at 37° C. for 1 hour or at room temperature overnight.

(5) Empty plate and wash each well 3 times with PBS-T.

(6) Add 200 ul of 1/1,000 dilution in PBS-T of monoclonal antibody for Toxin A (PCG-4/B) to each well. Incubate plate at 37° C. for 1 hour.

(7) Empty plate and wash each well 3 times with PBS-T.

(8) Add 200 ul of 1/800 dilution (in PBS-T) of goat anti-mouse IgG coupled to alkaline phosphatase to each well. Incubate plate at 37° C. for 1 hour.

(9) Empty plate and wash each well 3 times with PBS-T.

(10) Add 200 ul of p-nitrophenylphosphate (1mg/ml in diethanolamine buffer) to each well. Incubate plate at room temperature for 1 hour.

(11) Add 20 ul of 5 N NaOH to each well to terminate the reaction.

(12) Mix contents of each well with 0.8 ml dH$_2$O (total volume of assay mixture ca. 1 ml) and measure the absorbance at 405 nm or direct read on a reader such as the ELIA available from Fisher Scientific.

In using a mixture of monoclonal antibody and polyclonal mono-specific antibody in Step 6 of the above assay procedure, in Step 8, the tracer is a mixture of goat anti-mouse IgG and rabbit anti-goat IgG, each labeled with alkaline phosphatase.

EXAMPLE VII

Latex agglutination (LA). Samples (0.5 ml) of latex beads (10% suspension: Difco Laboratories) and monoclonal antibody PCG-4 diluted in glycine-NaCl buffer, pH 8.2 were mixed and incubated for 2 h at 37° C. with occasional shaking. After incubation, 0.25 ml of glycine-NaCl buffer containing 0.5% bovine albumin and 0.1% NaN$_3$ was added to each mixture, and the sensitized beads were stored at 4° C. The LA assay was performed by mixing samples (20 ul) of toxin A diluted in PBS and sensitized beads on a ring slide for 5 min at room temperature, and observing the suspension for macroscopic agglutination.

EXAMPLE VIII

Preparation of monospecific toxin A Antiserum. A 1-year-old, Alpine/Nubian male goat was injected with toxoid A mixed 1:1 with incomplete Freund adjuvant. The goat received about 1 mg of toxoid A subcutaneously once each week for 4 weeks. The animal was then injected with active toxin A bound to Affi-Gel 10 (Bio-Rad Laboratories). The goat received 1 ml of a 10% suspension of the toxin A-gel (about 0.1 mg of toxin A protein) once each week for 6 weeks. The antiserum was brought to 50% saturation with a solution of 100% saturated (NH$_4$)$_2$SO$_4$. The precipitate was collected, dissolved in PBS to the original sample volume, and dialyzed against PBS. The preparation was passed through 0.45 um membrane and stored at 4° C.

EXAMPLE IX

This example is directed to the production of both mono-specific antibody for toxin A, and mono-specific antibodies for toxin B.

Bacteria and growth conditions. Two-liter brain heart infusion dialysis tube flasks were inoculated with 0.1 ml of actively growing cultures of *C. difficile* VPI strain 11186 (non-toxigenic) and *C. difficile* VPI strain 10463 (toxigenic), and the flasks were incubated at 37° C. for 3 days. The cells were obtained from inside the dialysis sack by centrifugation of the contents (9,000 xg for 15 minutes).

Preparation of boiled cell wash (BCW)—Sepharose, Toxin A—(ToxA)—Sepharose, and Toxin B (ToxB-)—Sepharose.

Strain 10463 packed cells (ca. 15 ml obtained from 12 flasks) were washed 3 times (30 ml per wash) with 0.1M NaHCO$_3$-0.5M NaCl pH8. Cell washes were pooled and the pool was heated at 100° C. for 15 minutes. The precipitated material was removed by centrifugation (12,000× g for 30 minutes) and the supernatant fluid (ca. 34 mg. of protein in 90 ml) was added to 60 ml of Sepharose 4 B (Pharmacia Fine Chemicals, Uppsala, Sweden) which had been activated with 18 g of CNBr. The suspension was gently mixed at 4° C. overnight and uncoupled material was removed by washing the gel with one bed volume of 0.1M NaHCO$_3$-0.5M NaCl. Protein analysis of the wash indicated that the gel preparation contained ca. 0.3mg of protein per ml gel. The remaining active groups on the Sepharose gel were blocked by adding one bed volume of 1M ethanolamine, pH 8, and mixing the gel at 4° C. overnight. The gel, designated BCW-Sepharose, was washed 4 X with alternating volumes (2 bed volumes per wash) of 0.1M sodium acetate-0.5M NaCl, pH 4, and 0.1M NaHCO$_3$-0.5M NaCl, pH 8.

Partially purified toxin A and toxin B were prepared by ion exchange chromatography on DEAE Sepharose CL-6B (Pharamcia Fine Chemicals) as described in Example II and each preparation was dialyzed overnight at 4° C. against 0.1M NaHCO$_3$-0.5M NaCl. Toxin A (ca. 3.3 mg of protein in 20 ml) and toxin B (ca. 1.1 mg of protein in 20 ml) were each coupled, as described for BCW-Sepharose, to 20 ml of Sepharose 4 B which had been activiated with 7 g of CNBr. Protein analysis of the washes indicated that ToxA-Sepharose and ToxB-Sepharose contained 170 ug of protein and 54 ug of protein per ml of gel, respectively.

Purification of monspecific antisera against Toxins A and B. Goat antiserum was prepared, as previously described, using refrigerated formaldehyde (Ehrich, M., R. L. Van Tassell, J. M. Libby, and T. D. Wilkins, 1980. Production of *Clostridium difficile* antitoxin. Infect. Immun. 28:1041–1043.) against a crude *C. difficile* toxin preparation containing Toxins A and B. Antiserum (5 ml) was added to a suspension of strain 11186 cells (1.5 ml packed cells in 3 ml 0.85% NaCl) and the mixture was gently homogenized with a Potter Elvehjam tissue grinder and then rotated for 2 h at room temperature. The cells were subsequently removed by centrifugation (12,000×g for 30 min) and the supernatant fluid was passed through a 0.45 um membrane and concentrated to 1 X with a minicon-B15 concentrator (Amicon Corp., Lexington Mass.). Strain 11186 cell-adsorbed antiserum (4.1 ml) was applied to a column (1.5 by 31.4 cm) of BCW-Sepharose, and nonadsorbed material was eluted at room temperature with 2 bed volumes of 0.1M $NaHCO_3$-0.5M NaCl, pH 8, at a flow rate of 40 ml/h. The eluate was concentrated to 1 X by ultrafiltration in a stirred cell equipped with a PM 10 membrane (Amicon Corp.). The BCW-Sepharose-eluate (4.1 ml) was divided into 2 equal portions which were applied to columns (1 by 25 cm) of ToxA-Sepharose and ToxB-Sepharose. Nonadsorbed material was eluted at room temperature from each column with 2 bed volumes of 0.1M $NaHCO_3$-0.5M NaCl, pH 8, at a flow rate of 40 ml/h. Eluates were concentrated to 1 X by ultrafiltration.

Elution of antibodies bound to ToxA-Sepharose and ToxB-Sepharose. Following the elution of nonadsorbed material from ToxA-Sepharose and ToxB-Sepharose, the columns were washed with 0.1M $NaHCO_3$-0.5M NaCl., pH 8, until there was no measurable adsorbance at 280 mn. Antibodies bound to the gels were eluted by applying 5 ml of 3.5M KSCN, pH 6.8, to each column and washing with 0.1M $NaHCO_3$-0.5M NaCl. Approximately 2 bed volumes were collected from each column. The eluates were dialyzed against 41 of 0.1M borate-buffered saline pH 8.5, at 4° C. overnight and concentrated to 1 X by ultrafiltration.

The antibody eluted from the ToxA-Sepharose column is the mono-specific antibody for toxin A of *C. difficile* and the antibody eluted from the ToxB-Sepharose column is the monospecific antibody for toxin B of *C. difficile.*

Purification of IgG fraction. The eluted antibodies from the ToxA-Sepharose and ToxB-Sepharose column were purified by chromatography on DEAE Affi-Gel Blue (Bio-Rad Laboratories, Rockville Centre, NY) as recommended by the manufacturer for the purification of rabbit IgG. Antiserum samples (2 ml) were applied to a column of DEAE Affi-Gel Blue (1 by 31.8 cm) and eluted at a flow rate of 20ml/h. Fractions (2 ml) containing purified IgG were pooled and concentrated to 1 X by ultrafiltration.

Example X

This example is directed to production of pure toxin A of *C. difficile.*

Bacterial strain. Clostridium difficile VPI strain 10463was grown in two liter brain heart infusion (BHI) dialysis flasks for 72 hours at 37° C. After centrifuation at 8000 X g for 10 minutes and filtration through a 0.45 um membrane filter (Millipore Corp., Bedford, MA), the culture supernatant (c. 750 ml) was concentrated to 50 ml by ultrafiltration, at 4° C., using an XM-100 membrane filter (Amicon Corp., Lexington, MA) with a thin channel type concentrator. The retentate was washed with 1500 ml of 50 mM TRIS-HCl buffer, pH 7.5 (4° C.) and concentrated to a final volume of 40–50 ml. This removed many small molecular weight contaminants. The concentrated supernatant was loaded onto a 2.5 by 10 cm DEAE Sepharose CL-6 B column which had been equilibrated with 50 mM TRIS-HCl, pH 7.5. After sample loading, the column was washed with 200 ml of 50 mM TRIS-HCl, pH 7.5, containing 0.05M NaCl. The sample was eluted first with a 300 ml linear NaCl gradient in 50 mM Tris-HC1 buffer (0.05–0.25M NaCl), followed by 150 ml of 50 mM TRIS-HC1, pH 7.5, containing 0.3M NaCl. A second 300 ml linear gradient (0.3–0.6M NaCl) in the same buffer followed the 0.3M NaCl wash. The flow rate of the columns was 55–60ml per hr (Gravity) at 4° C. Fractions (4.2 ml) were collected and assayed for cytotoxicity using CHO-K1 cells.

The fractions containing the highest cytotoxic titers were pooled, filter-sterilized and stored at 4° C. The toxins that eluted in the first and second NaCl gradients were designated Toxins A and B respectively, and are partially purified toxins A and B, respectively.

Five to ten ml of the toxic fractions from the first DEAE gradient (Toxin A) were dialyzed against one liter of 0.01M sodium acetate buffer pH 5.5 at 4° C. for 18–24 hours. The dialysate was centrifuged to recover the precipitate at 169 × g for 10 minutes and was then washed with 5 ml of the same acetate buffer and centrifuged again. The precipitate was solubilized in 5–10 ml of 50 mM TRIS-HC1, pH 7.5 containing 0.05M NaCl and the solution of purified toxin A was filter-sterilized and stored at 4° C.

Although the monoclonal antibody for toxin A is preferably employed in an assay for *C. difficile* it is to be understood that the scope of the invention is not limited to such use.

It is also to be understood that the assay for toxin A is also in fact an assay for *C. difficile* disease in that toxin A is present during such disease.

Numerous modifications and variations of the present invention are possible in light of the above teachings and, therefore, within the scope of the appended claims, the invention may be practiced otherwise than as particularly described.

What is claimed is:

1. Monoclonal antibody for toxin A of *C. difficile* which immunoprecipitates toxin A of *C. difficile.*

2. A composition, comprising:

a solid support sensitized with the antibody of claim 1.

3. The monoclonal antibody of claim 1 wherein the monoclonal antibody is produced from a hybridoma having Accession Number ATCC HB 8713.

4. The monoclonal antibody of claim 1 wherein the monoclonal antibody is produced from a hybridoma having ATCC HB 8712.

5. The monoclonal antibody of claim 1 wherein the monoclonal antibody has a molecular weight of about 160,000 as determined by polyacrylamide gel electrophoresis.

6. The antibody of claim 1 wherein the antibody neutralizes, in vitro, the enterotoxin activity of toxin A.

7. The monoclonal antibody of claim 1 wherein the antibody prevents the binding of toxin A to rabbit erythro-cytes.

8. A hybridoma which produces the antibody of claim 1.

9. The hybridoma of claim 8 wherein the hybridoma has Accession Number ATCC HB 8713.

10. The hybridoma of claim 8 wherein the hybridoma has Accession Number ATCC HB 8712.

11. In an assay for toxin A of *C. difficile* wherein an analyte containing toxin A is contacted with an antibody, and subsequently the presence of toxin A is detected in said analyte, the improvement comprising:
contacting said analyte with the monoclonal antibody of claim 1 to bind only toxin A to said monoclonal antibody.

12. The assay of claim 11 wherein the analyte is contacted with both said monoclonal antibody on a solid support and said monoclonal antibody in a labeled form.

13. The assay of claim 11 wherein in the assay antibody to *C. difficile* is supported on a solid support, the supported *C. difficile* antibody is contacted with analyte to bind *C. difficile* antigen to the supported *C. difficile* antibody and subsequently the bound antigen is contacted with monoclonal antibody in a labelled form and the presence of said toxin is determined by detecting the presence of bound label.

14. The assay of claim 13 wherein the label is an enzyme label.

15. The assay of claim 13 wherein the label is a radioactive label.

16. The assay of claim 11 wherein in the assay antibody to *C. difficile* is supported on a solid support, the supported *C. difficile* antibody is contacted with analyte to bind the *C. difficile* antigen to the *C. difficile* antibody, the antigen is contacted with monoclonal antibody to bind monclonal antibody to toxin A of the bound antigen, subsequently bound monoclonal antibody is contacted with a labelled form of antibody for the monoclonal antibody, and the presence of said toxin A is determined by detecting the presence of bound label.

17. The assay of claim 16 wherein the label is an enzyme label.

18. The assay of claim 17 wherein the label is a radioactive label.

19. The assay of claim 18 wherein the analyte is contacted with both said monoclonal antibody on a solid support and said antibody mixture containing a labeled form of the polyclonal antibody and the monoclonal antibody.

20. In an assay for toxin A of *C. difficile* wherein an analyte containing toxin A is contacted with an antibody, and subsequently the presence of toxin A is detected in said analyte, the improvement comprising
contacting said analyte with an antibody mixture of the monoclonal antibody of claim 1 and polyclonal monospecific antibody for toxin A to bind only toxin A to said antibody mixture.

21. The assay of claim 20 wherein in the assay antibody to *C. difficile* is supported on a solid support, the supported *C. difficile* antibody is contacted with analyte to bind *C. difficile* antigen to the supported *C. difficile* antibody and subsequently the bound antigen is contacted with said mixture of monoclonal antibody and polyclonal mono-specific antibody both in a labelled form and the presence of said toxin is determined by detecting the presence of bound label.

22. The assay of claim 21 wherein the label is an enzyme label.

23. The assay of claim 21 wherein the label is a radioactive label.

24. The process of claim 20 wherein in the assay antibody to *C. difficile* is supported on a solid support, the supported *C. difficile* antibody is contacted with analyte to bind the *C. difficile* antigen to the *C. difficile* antibody, the antigen is contacted with said antibody mixture of monoclonal antibody and polyclonal mono-specific antibodies for toxin A to bind said mixture to toxin A of the bound antigen, said bound antibody mixture is contacted with a mixture of the labelled form of antibody for the mono-specific antibody and a labelled form of antibody for the monoclonal antibody, and the presence of said toxin A is determined by detecting the presence of bound label.

25. The assay of claim 24 wherein the label is an enzyme label.

26. The assay of claim 25 wherein the enzyme label is alkaline phosphatase.

27. An assay for *C. difficile* comprising:
contacting a sample containing toxin A of *C. difficile* with solid particles sensitized with the monoclonal antibody of claim 1 and detecting the presence of toxin A by agglutination of the sensitized particles.

28. The assay of claim 27 wherein the particles are sensitized with a mixture of said monoclonal antibody and a polyclonal monospecific antibody for toxin A of *C. difficile*.

29. Mono-specific antibody for toxin A of *C. difficile*.

30. A composition, comprising:
a solid support sensitized with the mono-specific antibody of claim 26.

31. Mono-specific antibody for toxin B of *C. difficile*.

32. A composition, comprising:
a solid support sensitized with the mono-specific antibody of claim 31.

33. Antibody specific for toxins of *C. difficile*.

34. A composition, comprising:
a solid support sensitized with the antibody of claim 33.

* * * * *